(12) United States Patent
Tsai et al.

(10) Patent No.: US 8,529,575 B2
(45) Date of Patent: Sep. 10, 2013

(54) SURGICAL CLAMP

(75) Inventors: Yung-Fang Tsai, Taichung (TW);
Wei-Kai Wang, Changhua (TW);
Yung-Fu Liao, Caotun Township,
Nantou County (TW); Din-Hsiang Tseng, Changhua (TW)

(73) Assignee: Intai Technology Corp., Taichung (TW)

( * ) Notice: Subject to any disclaimer, the term of this patent is extended or adjusted under 35 U.S.C. 154(b) by 212 days.

(21) Appl. No.: 13/206,573

(22) Filed: Aug. 10, 2011

(65) Prior Publication Data
US 2012/0197291 A1 Aug. 2, 2012

(30) Foreign Application Priority Data

Jan. 31, 2011 (TW) .............................. 100103606 A

(51) Int. Cl.
*A61B 17/17* (2006.01)
(52) U.S. Cl.
USPC ............................................. 606/89; 606/96
(58) Field of Classification Search
USPC ................. 606/102, 119, 139, 144, 147, 205,
606/206, 207, 208, 96–98, 104, 105; 81/314,
81/342, 416
See application file for complete search history.

(56) References Cited

U.S. PATENT DOCUMENTS

| | | | | |
|---|---|---|---|---|
| 3,019,790 A | * | 2/1962 | Militana | 606/108 |
| 8,236,001 B2 | * | 8/2012 | Willi et al. | 606/89 |
| 2003/0212435 A1 | * | 11/2003 | Gold et al. | 606/206 |
| 2004/0176779 A1 | * | 9/2004 | Casutt et al. | 606/102 |
| 2008/0215057 A1 | * | 9/2008 | Willi et al. | 606/88 |

* cited by examiner

*Primary Examiner* — Tuan V Nguyen
(74) *Attorney, Agent, or Firm* — Alan Kamrath; Kamrath IP Lawfirm, P.A.

(57) ABSTRACT

A surgical clamp includes first and second supports respectively having first and second engagement sections. The first and second supports are pivotably connected at a connection by a pivotal portion such that the first and second supports are pivotable about a pivot axis extending through the connection. An opening is defined between the first and second engagement sections for receiving a bone of a patient. A connecting tube includes a first end fixed to the connection. A guiding tube includes an end connected to a second end of the connecting tube and is located in a central plane of the opening between the first and second engagement sections. The central plane includes the pivot axis and has equal spacing to the first and second engagement sections. A sliding rod is fixed to the connecting tube and includes a sliding groove slideably receiving a pole located on the pivotal portion.

8 Claims, 7 Drawing Sheets

SURGICAL CLAMP

BACKGROUND OF THE INVENTION

The present invention relates to a surgical clamp and, more particularly, to a surgical clamp including an operation guiding device for reliably guiding a guiding needle so that a surgical worker can immediately use a drilling device while achieving precise positioning during a surgical operation.

With reference to FIG. 1, during a surgical operation, a surgical worker operates a surgical clamp 50 to hold a bone 60 of a patient with one hand and operates an operation guiding device 70 and a guiding needle 80 with the other hand, which is troublesome and laborsome. The time and space required for operation are increased, which causes adverse affect to surgical operations in which every second counts. The bone 60 of the patient must be fixed by the surgical clamp 50 before drilling a hole in the bone 60 for subsequent insertion of a bone nail. Furthermore, care must be taken to avoid a large incision area in the surgical site of the patient. However, the sight of the surgical worker may be blocked by the surgical clamp 50 and the operation guiding device 70. The hole will not be located in a central plane of the bone 60 if the operation guiding device 70 is not located in the central plane of an opening of the surgical clamp 50. The bone nail is liable to be inserted to an offset position, imparting uneven force to the bone 60 during the healing stage. The bone 60 may even break after insertion of the bone nail if the offset of the bone nail is large.

A surgical worker generally has to operate several surgical devices at the same time in a surgical operation, and operation of each surgical procedure must be completed. Thus, the surgical operation in which every second counts may fail just because of an additional movement for operating one of the surgical devices.

Thus, a need exists for novel surgical clamp that allows the surgical operation to proceed faster and more reliable while reducing mistakes during the surgical operation.

BRIEF SUMMARY OF THE INVENTION

An objective of the present invention is to provide a surgical clamp that can be operated with a single hand, such that the surgical operation can proceed faster and more reliable while reducing mistakes during the surgical operation.

The present invention fulfills the above objective by providing a surgical clamp including a clamp body having first and second supports. The first support includes a first handle on a rear end thereof and a first engagement section on a front end thereof. The second support includes a second handle on a rear end thereof and a second engagement section on a front end thereof. The first and second supports are pivotably connected to each other at a connection by a pivotal portion. An opening is defined between the first and second engagement sections and adapted for receiving a bone of a patient. The first and second supports are pivotable to each other about a pivot axis extending through the connection for proceeding with clamping and opening movement. The first and second engagement sections are adapted to clamp the bone of the patient. An operation guiding device includes a connecting tube, a guiding tube, and a sliding rod. The connecting tube includes a first end fixed to the connection. The guiding tube includes an end connected to a second end of the connecting tube. The guiding tube is located in a central plane of the opening between the first and second engagement sections. The central plane includes the pivot axis and has equal spacing to the first and second engagement sections. The sliding rod is fixed to the connecting tube and includes a sliding groove slideably receiving a pole located on the pivotal portion.

By such an arrangement, during the opening and clamping movement of the first and second supports, the guiding tube is stably located in the central plane between the first and second engagement sections such that a surgical worker can operate a guiding needle faster and can reliably position the guiding needle, reducing mistakes during the surgical operation.

In a form shown, the inner tube is removably received in the guiding tube. Thus, the inner tube can be replaced with another inner tube according to the needs of different surgical operations.

In a form shown, the end of the guiding tube is pivotably connected to the second end of the connecting tube. Thus, an angle of between the guiding tube and the connecting tube can be adjusted during a surgical operation.

The present invention will become clearer in light of the following detailed description of illustrative embodiments of this invention described in connection with the drawings.

DETAILED DESCRIPTION OF THE INVENTION

Figure 1:
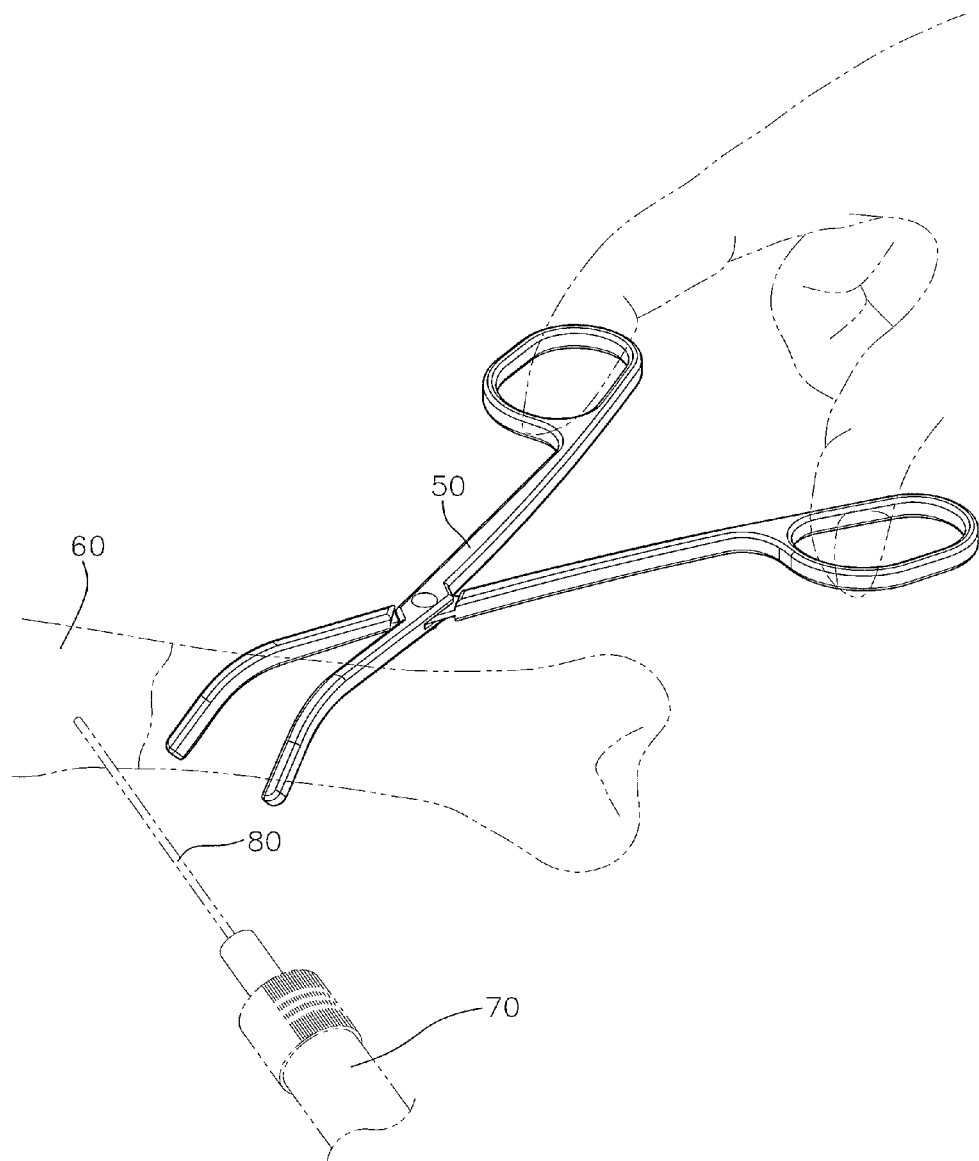
FIG. 1 shows a perspective view illustrating use of a conventional surgical clamp.
Figure 2:
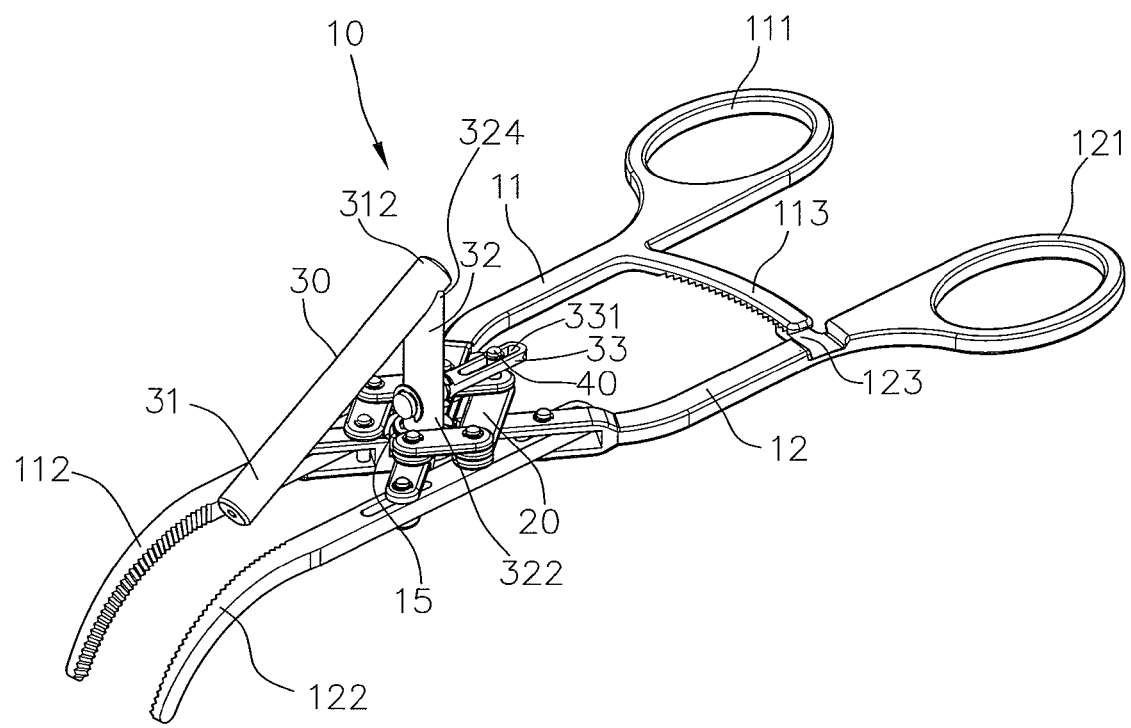
FIG. 2 shows a perspective view of a first example of a surgical clamp according to the present invention.
Figure 3:
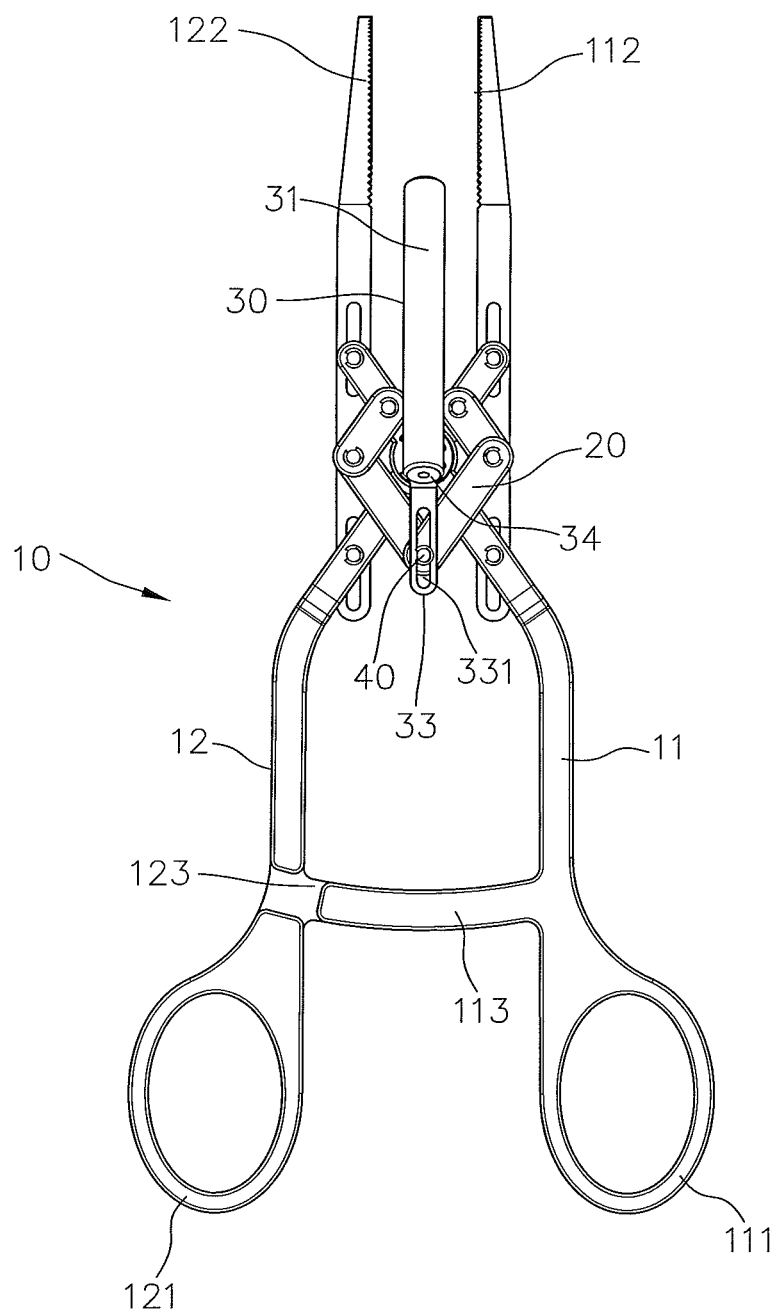
FIG. 3 shows a top view of the surgical clamp of FIG. 2.
Figure 4:
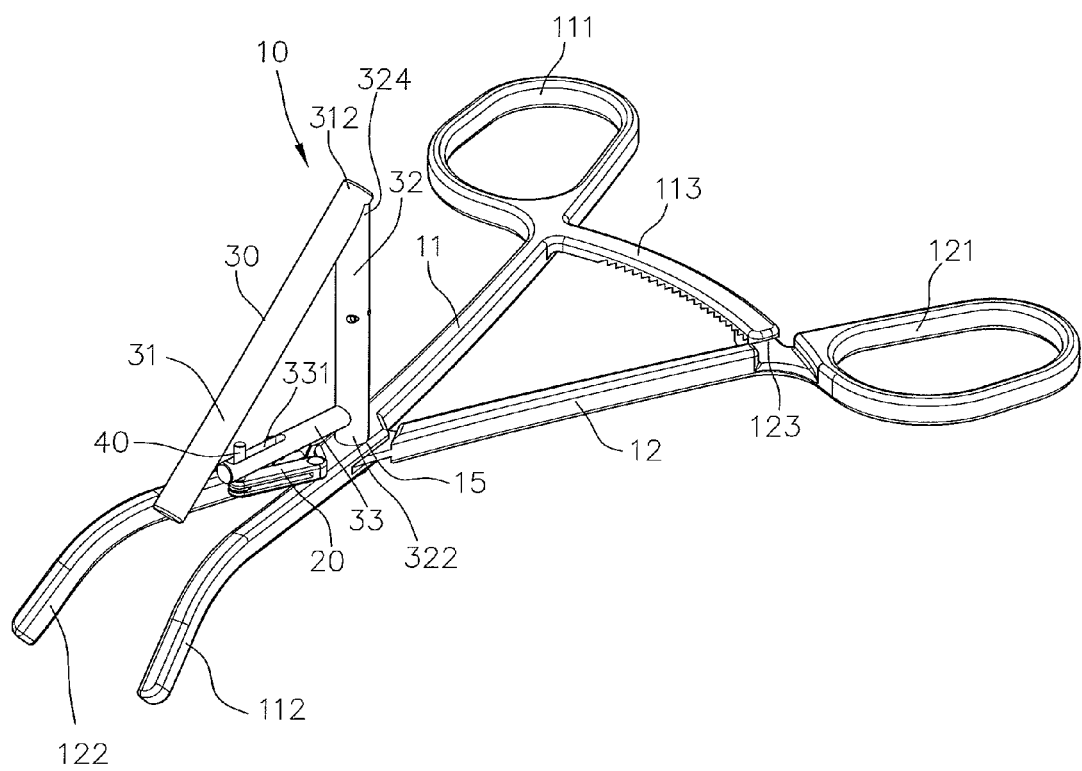
FIG. 4 shows a perspective view of a second example of the surgical clamp according to the present invention.
Figure 5:
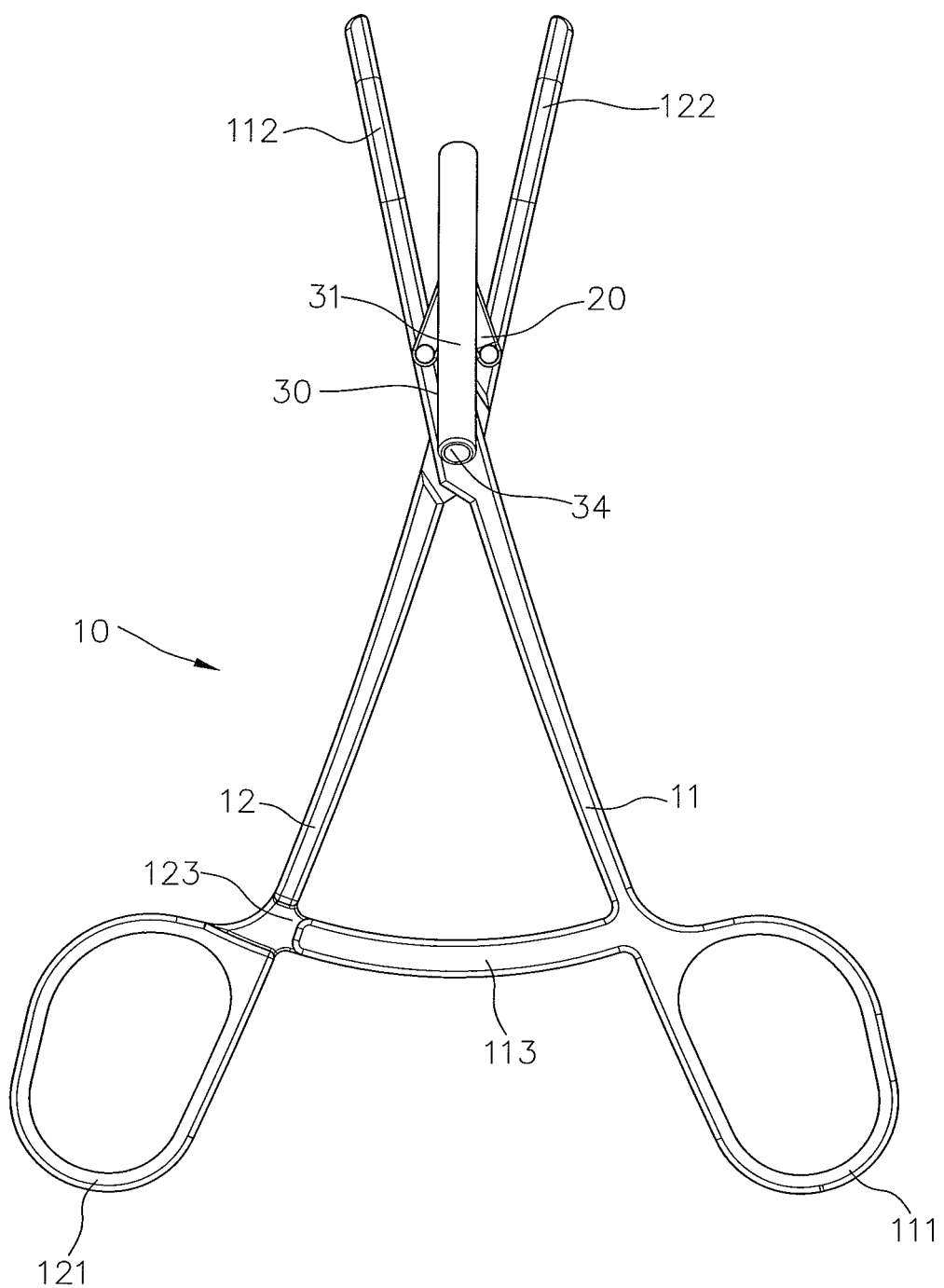
FIG. 5 shows a top view of the surgical clamp of FIG. 4.
Figure 6:
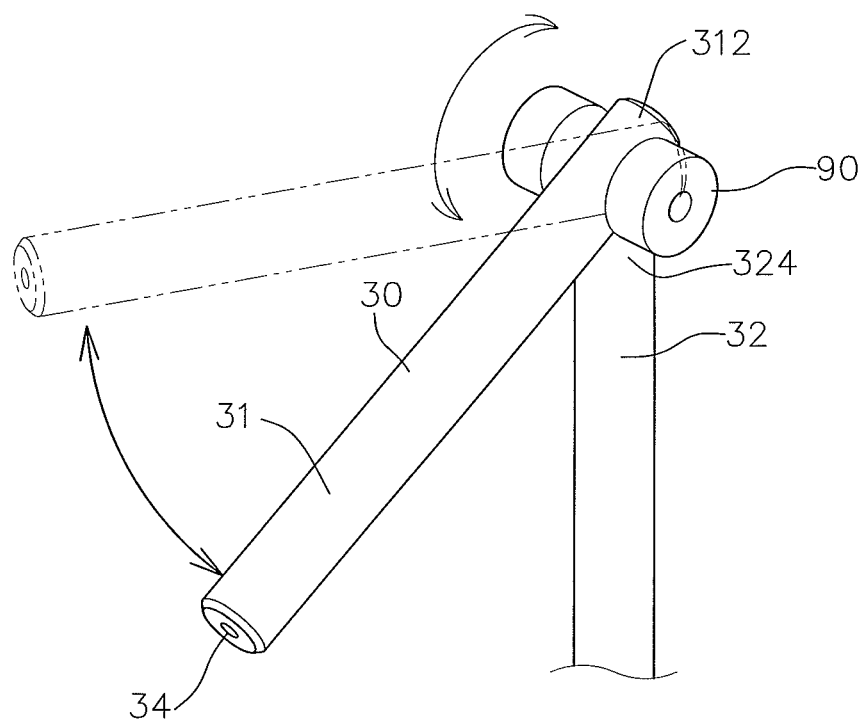
FIG. 6 shows a perspective view of a modified example of an operation guiding device of the surgical clamp according to the present invention.

A surgical clamp according to the present invention is shown in FIGS. 2-7. In the forms shown in FIGS. 2-5, the surgical clamp includes a clamp body 10 having first and second supports 11 and 12. A first handle 111 is provided on a rear end of the first support 11. A second handle 121 is provided on a rear end of the second support 12. The first and second supports 12 are pivotably connected to each other at a connection 15 by a pivotal portion 20, allowing the first and second supports 11 and 12 to proceed with clamping and opening movement by pivoting the first and second supports 11 and 12 about a pivot axis extending through the connection 15.

Figure 7:
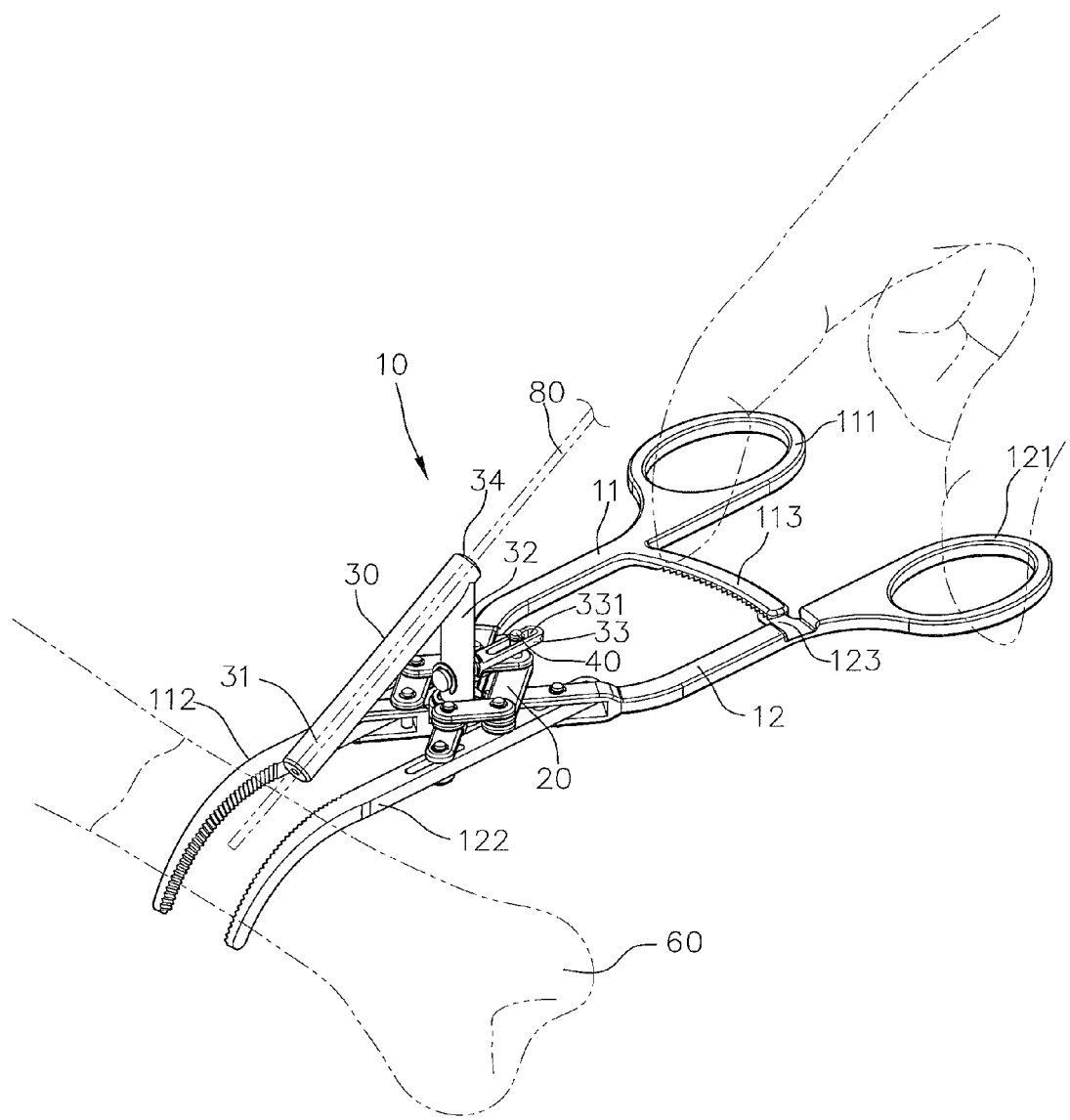
FIG. 7 is a perspective view illustrating use of the surgical clamp according to the present invention.

In the forms shown in FIGS. 2-5, a first engagement section 112 is provided on a front end of the first support 11. A second engagement section 122 is provided on a front end of the second support 12. An opening is defined between the first and second engagement sections 112 and 122 for receiving a bone 60 of a patient (FIG. 7). In the form shown in FIGS. 2 and 3, the pivotal portion 20 is of parallel type. Specifically, the first and second engagement sections 112 and 122 remain parallel to each other while moving towards each other for clamping the bone 60 of a patient. In the form shown in FIGS. 4 and 5, the pivotal portion 20 is of cross type. Specifically, an acute angle between the first and second engagement sections 112 and 122 decreases while moving towards each other for clamping the bone 60 of a patient.

In the forms shown in FIGS. 2-5, a first fixing portion 113 is provided on the rear end of the first support 11, and a second fixing portion 123 is provided on the rear end of the second support 12. The first and second fixing portions 113 and 123 can be releasably engaged with each other. The surgical clamp is fixed when the first and second fixing portions 113 and 123 engage with each other.

In the forms shown in FIGS. 2-6, the surgical clamp further includes an operation guiding device 30. The operation guiding device 30 includes a connecting tube 32 having a first end 322 fixed to the connection 15 and a guiding tube 31 having an end 312 connected to a second end 324 of the connecting tube 32. The guiding tube 31 is located in a central plane of the opening between the first and second engagement sections 112 and 122. The central plane includes the pivotal axis and has equal spacing to the first and second engagement sections 112 and 122. An inner tube 34 is removably received in the guiding tube 31. The inner tube 34 can be replaced with another inner tube according to the needs of different surgical operations. The operation guiding device 30 further includes a sliding rod 33 fixed between the first and second ends 322 and 324 of the connecting tube 32 and extending perpendicularly to the pivotal axis. The sliding rod 33 includes a sliding groove 331. A pole 40 is located on the pivotal portion 20 and slideably received in the sliding groove 331. In the form shown in FIGS. 2 and 3, the sliding rod 33 is extended through the connecting tube 32 and has a portion located between the connecting tube 32 and the first and second handles 111 and 112. In the form shown in FIGS. 4 and 5, the sliding rod 33 has an end fixed to the connecting tube 32 and is located between the connecting tube 32 and the first and second engagement sections 112 and 122. In the form shown in FIGS. 2-5, the end 312 of the guiding tube 31 is fixed to the second end 324 of the connecting tube 32. In the form shown in FIG. 6, the end 312 of the guiding tube 31 is pivotably connected to the second end 324 of the connecting tube 32 by at least one screw 90. Thus, an angle between the guiding tube 31 and the connecting tube 32 can be adjusted during the surgical operation. In the form shown in FIG. 6, the angle between the guiding tube 31 and the connecting tube 32 can be adjusted in a range between 20° and 180°.

FIG. 7 shows use of the surgical clamp according to the present invention. The first and second handles 111 and 121 of the first and second supports 11 and 12 are moved towards each other such that the first and second engagement sections 112 and 122 move towards each other to clamp a bone 60 of a patient. The sliding rod 33 and the pole 40 slide relative to each other due to provision of the sliding groove 331. A surgical worker can insert a guiding needle 80 through the guiding tube 31 into the bone 60 of the patient. During the opening and clamping movement of the first and second supports 11 and 12, the operation guiding device 30 is stably located in the central plane between the first and second engagement sections 112 and 122. Thus, the guiding tube 31 is precisely located in the central plane of the clamp body 10 such that the surgical worker can operate the guiding needle 80 faster and can reliably position the guiding needle 80, reducing mistakes during the surgical operation.

Although specific embodiments have been illustrated and described, numerous modifications and variations are still possible without departing from the essence of the invention. The scope of the invention is limited by the accompanying claims.

The invention claimed is:

1. A surgical clamp comprising:
a clamp body including first and second supports, with the first support including a first handle on a rear end thereof and a first engagement section on a front end thereof, with the second support including a second handle on a rear end thereof and a second engagement section on a front end thereof, with the first and second supports pivotably connected to each other at a connection by a pivotal portion, with an opening defined between the first and second engagement sections, with the opening adapted for receiving a bone of a patient, with the first and second supports pivotable to each other about a pivot axis extending through the connection for proceeding with clamping and opening movement, with the first and second engagement sections adapted to clamp the bone of the patient;
an operation guiding device including a connecting member, a guiding tube, and a sliding rod, with the connecting member including a first end fixed to the connection and a second end, with the guiding tube including an end connected to the second end of the connecting member, with the end of the guiding tube pivotably connected to the second end of the connecting member, with an angle between the guiding tube and the connecting member being adjustable, with the guiding tube located in a central plane of the opening between the first and second engagement sections, with the central plane including the pivot axis and having equal spacing to the first and second engagement sections, with the sliding rod fixed to the connecting member and including a sliding groove; and
a pole located on the pivotal portion, with the pole slideably received in the sliding groove.

2. The surgical clamp as claimed in claim 1, with the first support including a first fixing portion on the rear end thereof, with the second support including a second fixing portion on the rear end thereof, with the first and second fixing portions releasably engaged with each other, with the surgical clamp being fixed when the first and second fixing portions engaged with each other.

3. The surgical clamp as claimed in claim 1, further comprising: an inner tube removably received in the guiding tube.

4. The surgical clamp as claimed in claim 1, with the sliding rod extending through the connecting member and having a portion located between the connecting member and the first and second handles.

5. The surgical clamp as claimed in claim 1, with the sliding rod located between the connecting member and the first and second engagement sections and having an end fixed to the connecting member.

6. The surgical clamp as claimed in claim 1, with the end of the guiding tube fixed to the second end of the connecting member.

7. The surgical clamp as claimed in claim 1, with the pivotal portion being parallel configuration with the first and second engagement sections remaining parallel while moving together.

8. The surgical clamp as claimed in claim 1, with the pivotal portion being cross configuration with an angle between the first and second engagement sections decreasing while moving toward each other.

* * * * *